(12) United States Patent
Blagg et al.

(10) Patent No.: US 9,486,550 B2
(45) Date of Patent: Nov. 8, 2016

(54) DISPOSABLE ELECTRICAL EMANATION DEVICES

(71) Applicant: Reckitt & Colman (Overseas Limited), Slough, Berkshire (GB)

(72) Inventors: Adrian Blagg, Hull (GB); Avijit Das, Hull (GB); Kristian Matthews, Hull (GB)

(73) Assignee: Reckitt & Colman (Overseas) Limited, Slough, Berkshire (GB)

(*) Notice: Subject to any disclaimer, the term of this patent is extended or adjusted under 35 U.S.C. 154(b) by 0 days.

(21) Appl. No.: 14/404,852

(22) PCT Filed: May 30, 2013

(86) PCT No.: PCT/GB2013/051431
§ 371 (c)(1),
(2) Date: Dec. 1, 2014

(87) PCT Pub. No.: WO2013/179036
PCT Pub. Date: Dec. 5, 2013

(65) Prior Publication Data
US 2015/0125137 A1 May 7, 2015

(30) Foreign Application Priority Data
May 30, 2012 (GB) .................................. 1209607.9

(51) Int. Cl.
*A61M 16/00* (2006.01)
*F24F 3/14* (2006.01)
(Continued)

(52) U.S. Cl.
CPC ............... *A61L 9/03* (2013.01); *A01M 1/2077* (2013.01)

(58) Field of Classification Search
CPC ............................. A61L 9/03; A01M 1/2077
USPC ................. 392/386, 389, 390–393, 402, 403
See application file for complete search history.

(56) References Cited

U.S. PATENT DOCUMENTS 5,111,477 A * 5/1992 Muderlak ............ H05B 1/0225
392/390
5,903,710 A * 5/1999 Wefler .................... A61L 9/037
239/47

(Continued)

FOREIGN PATENT DOCUMENTS

GB 2117639 A 10/1983
GB 2302507 A 1/1997

(Continued)

OTHER PUBLICATIONS

International Search Report for PCT/GB2013/051431 dated Oct. 7, 2013.

*Primary Examiner* — Dana Ross
*Assistant Examiner* — Lindsey C Teaters
(74) *Attorney, Agent, or Firm* — Norris McLaughlin & Marcus PA

(57) ABSTRACT

An emanation device is described which comprises a housing defining a sealed container having a front wall and a rear wall defining the length and width of the housing and connected to each other by a top wall, a bottom wall and one or more side walls defining the depth of the housing, wherein the length and width are each greater than the depth; one or more vent holes in the housing; electrical plug pins connected to the rear wall of the housing, said plug pins being operatively connected to a heating means located within the interior of the housing; an absorbent pad containing a quantity of air treatment agent mounted within the interior of the housing; wherein the pad fills a majority of the length and width of the housing; and wherein the heating means is located in connection with or immediately adjacent to a central portion of the pad on the front face thereof where the front face of the pad is adjacent the front wall and remote from the face of the pad facing the rear wall and electrical plug pins.

17 Claims, 2 Drawing Sheets

(51) Int. Cl.
*F24F 6/00* (2006.01)
*A61H 33/12* (2006.01)
*D06F 75/00* (2006.01)
*F17C 7/04* (2006.01)
*A61L 9/03* (2006.01)
*A01M 1/20* (2006.01)

(56) References Cited

U.S. PATENT DOCUMENTS

| | | | | |
|---|---|---|---|---|
| 5,945,094 A | * | 8/1999 | Martin | A01M 1/2077 219/392 |
| 6,085,026 A | * | 7/2000 | Hammons | A61L 9/03 219/544 |
| 6,381,408 B1 | * | 4/2002 | Jaworski | A01M 1/2077 392/390 |
| 7,324,744 B2 | * | 1/2008 | Triplett | A61L 9/037 392/386 |
| 2003/0138241 A1 | * | 7/2003 | Pedrotti | A01M 1/2072 392/395 |
| 2004/0247300 A1 | * | 12/2004 | He | A01M 1/2072 392/390 |
| 2005/0286876 A1 | * | 12/2005 | Gasper | A01M 1/2077 392/392 |

FOREIGN PATENT DOCUMENTS

| | | |
|---|---|---|
| JP | 2000166452 A | 6/2000 |
| WO | 2010143153 A1 | 12/2010 |

* cited by examiner

DISPOSABLE ELECTRICAL EMANATION DEVICES

This is an application filed under 35 USC 371 of PCT/GB2013/051431, which in turn claims priority to GB 1209607.9 filed 30 May 2012.

FIELD OF THE INVENTION

The present invention to disposable electrical emanation devices that are configured to be inexpensive to manufacture and provide a user with a convenient means to emanate air treatment agents into the surrounding environment for a period of time before being disposed of and particularly, but not exclusively, for the emanation of air treatment agents in the form of air treatment agents such as fragrances, deodorizing and/or pest control materials.

BACKGROUND

Devices are known in which a bottle of air treatment agent has an upwardly projecting wick and a heater is located in the vicinity of the upper end of the wick to accelerate the evaporation of air treatment agent from the wick. The bottle, wick and heater are retained within a housing which carries an electric plug. To operate the heater the device is plugged into a wall socket. Devices of this type commonly claim to allow control of the rate of evaporation of the air treatment agents, for example, by varying the distance between the heater and the wick.

Known prior art devices suffer from the drawback of efficiency and convenience. Whilst these devices are capable of emanating large quantities of air treatment agent they generally use significant amounts of power, generally the heating element of such a device has a power consumption of greater than 2 W, and are not inexpensive to manufacture. Due to their inherent cost of manufacture it is necessary to provide replaceable refills of volatile to use with such devices. Clearly such devices are not suitable for use as a disposable device.

Furthermore, since the associated manufacturing costs of both the device and the replaceable refill intended for use with the device are not inexpensive, such devices are not suitable for use in many developing markets where the available household income is unlikely to be sufficient to support the purchase and the ongoing power consumption costs.

In addition, such devices are not suitable for use as a trial product such that a user can sample the effects of the emanated air treatment agent without necessarily committing to the not insignificant costs of the prior art device and associated replaceable refill.

The present invention intends to address the drawbacks discussed above.

SUMMARY OF INVENTION

According to the present invention there is provided therefore an emanation device comprising: a housing defining a sealed container having a front wall and a rear wall their area defining length and width of the housing and connected to each other by a top wall, a bottom wall and one or more side walls defining the depth of the housing, wherein the length and width are each greater than the depth; provided with at least one vent hole in each of the top wall, the bottom wall and the, or each, side wall;

electrical plug pins connected to the rear wall of the housing, said plug pins being operatively connected to a heating means located within the interior of the housing;

an absorbent pad containing a quantity of air treatment agent mounted within the interior of the housing;

wherein the pad fills a majority of the length and width of the housing;

and wherein the heating means is located in connection with or immediately adjacent to a central portion of the pad on the front face thereof where the front face of the pad is adjacent the front wall and remote from the face of the pad facing the rear wall and electrical plug pins.

Emanation devices according to the present invention are advantageous in that they provide a planar device of a generally shallow depth relative to how far the device as a whole protrudes outwardly from a mains electrical socket when engaged therewith during use. The location of the heating means on the side of the pad that is remote from the rear wall and plug pins is particularly advantageous as the pad is able to act as a heat insulator thus ensuring that the safe operation of the device despite its shallow depth without fear of the heat being transferred to the electrical socket. Also, the shallow depth of the device further improves the safety on the basis that the device will protrude away from the electrical socket less than prior art devices and will thus be less likely to be inadvertently knocked, bumped into or the like by passing footfall.

Furthermore the inventors of the present invention have realised that the prior art devices have been limited in the orientation with which they can be connected to electrical sockets. In particular, hitherto prior art emanation devices containing a pad or wick loaded with or connected to a reservoir of an air treatment agent generally held the heater toward one extremity of the pad/wick to ensure convection airflow permits adequate emanation. However, the inventors have realised further that despite the prior art it is possible to produce a device that may be used with an electrical socket in any orientation providing there is no external reservoir and the pad contains the entire quantity of air treatment agent and that the heating means is located in connection with or immediately adjacent to a central portion of the pad on the front face thereof such that regardless of the orientation there will be uniform emanation of the agent.

Advantageously, the location of the heating means in connection with or immediately adjacent to a central portion of the pad on the front face thereof ensures that there is zero to minimal heat loss due to air resistance between the heater and the pad thus ensuring that the device is energy efficient. Most preferably the heating means is in contact with the pad. Preferably the power consumption of the device of the present invention is <2 W, and more preferably <1.5 W, and even more preferably <1.2 W; hitherto prior art devices generally operated at >2 W.

The air treatment agent may be a volatile liquid, and preferably a volatile liquid containing one or more of: a fragrance, a deodorizing material and/or a pest control material.

Historically prior art emanation devices were not available for use in any orientation due to problems with air circulation and condensation, the latter problem often being alleviated by increasing the operating temperature of the heater but which affects the energy efficiency. To ensure energy efficiency of the devices of the present invention, the problem of condensation is preferably overcome by at least a portion of the pad being in contact with at least one of: the top wall, the bottom wall and/or the side wall(s), and more preferably by at least a portion of the pad being in contact with at least two of: the top wall, the bottom wall and/or the side wall(s), and even more preferably by at least a portion of the pad being in contact with the top wall, the bottom wall and the side wall(s); and most preferably the pad being in contact with all of the top wall, the bottom wall and the side wall(s). The pad may be provided with one or more castlations to facilitate the contact with the wall(s).

The device and consequently the pad held therewithin can be of any shape, however, generally a four sided shape is preferred. Electrical sockets, such as those used in the USA, are installed which would permit a device with electrical plug pins to be orientated in one of four orientations, therefore, by a four sided shape is generally preferred to ensure that the device is aligned with the electrical socket regardless of the orientation with which it is inserted. Even more preferably the device may be sized such that is it capable of blocking access to a standard sized adjacent electrical socket when connected to a socket.

The pad is preferably made from a material possessing absorbent, fire retardant and wicking properties, ideally the pad is made from melt blown polypropylene. Alternatively the pad may be provided by electrical conductive paper that has inlaid carbon to act as heating means due to being an electrically conductive which, upon an electric current being applied thereto, resistively heats to initiate or increase the emanation rate of the air treatment agent held within the conductive paper. In such an arrangement the electrically conductive paper could be provided in a folded configuration in order to increase the amount of air treatment agent that could be held within the device. The housing is provided with at least one vent hole in each of the top wall, the bottom wall and the, or each, side wall. This arrangement provides a twofold advantage over prior art devices in that, firstly, it urges chimney-effect airflow through the device to drive the emanation of the air treatment agent from the absorbent pad. Secondly the arrangement reduces the likelihood of condensation regardless of the orientation of the device during use. Preferably the vent holes are located such that when the plug pins are located in a mains electrical socket, the top vent hole(s) is located within the uppermost ⅓ of the top of the housing, the bottom vent hole(s) is located within the bottom ⅓ of the bottommost of the housing, and the side vent hole(s) is located within the nearest ⅓ of the side(s) of the housing.

Preferably the size of the vent holes is arranged to be sufficiently large to permit emanation therethrough without a build-up of condensation within the interior of the device and yet not sufficiently large that they pose an insertion risk (i.e. a risk of a child's finger or the like being inserted through the vent hole into the interior of the device). Accordingly the vent holes may be sized to extend at least 1 mm in any lateral direction whilst possessing a minimum area of 2 mm$^2$. Preferably to substantially resist the aforementioned insertion risk, no continuous area of any single vent hole shall describe a radius of greater than 5 mm, and more preferably no continuous area of any single vent hole shall describe a radius of greater than 4.5 mm; and most preferably no continuous area of any single vent hole shall describe a radius of greater than 4 mm.

The shape of the vent holes may also be relevant to ensuring airflow and condensation reduction, specifically the vent holes should not contain sharp or thin edges as such edges promote both airflow reduction and condensation, rather the edges of the vent holes should generally have a substantially rounded profile of continuous or variable curvature.

Optionally, one or more vent holes may be provided in the front wall to provide optimal airflow in case the device is operated in a horizontal orientation when connected to a electrical extension cable; the normal operating orientation being vertical when connected to a electrical socket located in a wall.

In a preferred arrangement the air treatment agent can contain a dye and the rear wall can be transparent or translucent such that a user can notice the colour change of the pad as the air treatment agent is emanated, thus providing the device with a visual end of life mechanism.

Preferably the device of the present invention is configured to provide continuous emanation of the air treatment agent for 1 week (7×24 hours of continuous emanation).

Any of the features described herein may be combined with any of the above aspects in any combination.

DESCRIPTION OF AN EMBODIMENT

An embodiment of the invention will now be described, by way of example only and with reference to the drawings in which.

Figure 1:
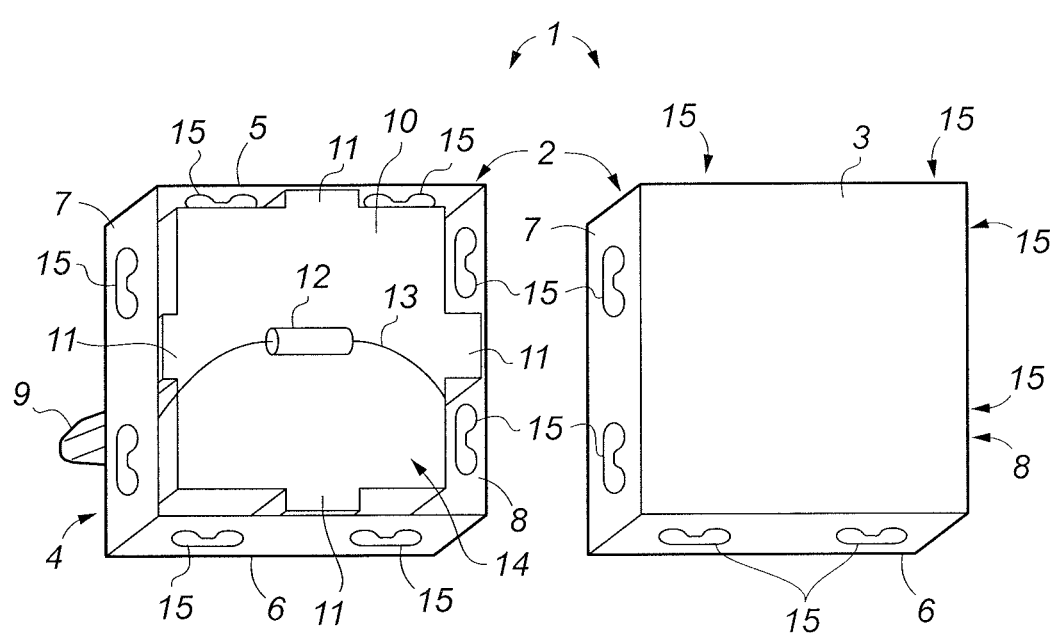
FIG. 1 shows an exploded view of the emanation device of the present invention.

FIG. 1 shows an exploded view of an emanation device 1 having a housing 2 which is made up of a front wall 3 a rear wall 4 which is connected to plug pins 9 (partially shown), and a top wall 5, a bottom wall 6 and side walls 7,8. The device 1 is, compared to prior art devices, generally planar and shallow wherein the length and width of the device are defined by the area of the front wall and rear wall 4 and the distance between these walls defines the depth, the distance being made up of the top 5, bottom 6 and side 7,8 walls of the housing 2, such that length and width are each greater than the depth.

A pad 10 made of a melt blown polypropylene is disposed in the interior of the housing 2. The pad has a quantity of air treatment agent absorbed therein. The pad 10 is shown as having a series of castlations 11 on each edge which permit any air treatment agent which condenses within the housing during use can be re-absorbed back into the pad 10 via one or more of the castlations 11 regardless of the orientation in which the device 1 is connected to a mains electrical socket.

A heating means 12 is provided electrically connected by wires 13 to the plug pins 9 and in contact with a front face 14 of the pad 10. The location of the heating means 12 on the front face 14 of the pad 10 ensures that the heating means 12 is located remote from the rear wall 4 and plug pins 9 permits the pad 10 to act as a heat insulator thus ensuring that the safe operation of the device 1 despite its shallow depth.

Vent holes 15 are provided in each of the top wall 5 (partially shown), the bottom wall 6 and each side wall 7,8 (partially shown), each vent hole being located within the uppermost, bottommost and nearest ⅓ respectively of the housing. The vent holes 15 are sized to be sufficiently large to permit emanation therethrough and to resist a build-up of condensation within the interior of the device and yet not sufficiently large that they pose an insertion risk (i.e. a risk of a child's finger or the like being inserted through the vent hole into the interior of the device). As the vent holes 15 may be sized to extend at least 1 mm in any lateral direction whilst possessing a minimum area of 2 mm². The shape of the vent holes 15 may also be relevant to ensuring airflow and condensation reduction, specifically the vent holes 15 should not contain sharp or thin edges as such edges promote both airflow reduction and condensation, rather the edges of the vent holes 15 should generally have a substantially rounded profile of continuous or variable curvature. These arrangements reduce the likelihood of condensation regardless of the orientation of the device 1 during use. Although not shown, the housing 2 will be sealed to prevent a user from accessing the interior of the device.

Although not shown, the heater and reservoir means 8 could be provided by electrical conductive paper that has inlaid carbon to act as heating means due to being an electrically conductive material which, upon an electric current being applied thereto, resistively heats to initiate or increase the emanation rate of the air treatment agent held within the conductive paper. In such an arrangement the electrically conductive paper could be provided in a folded configuration in order to increase the amount of air treatment agent that could be held within the device.

Figure 2:
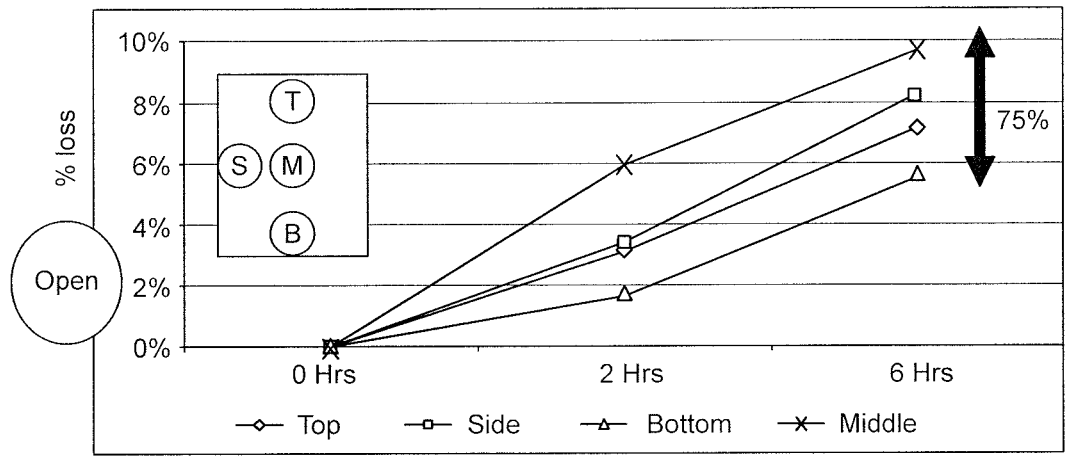
FIG. 2 shows a graph of performance variation associated with the location of the heating means relative to the absorbent pad.

Turning to FIG. 2 a weight-loss study is shown in which the position of the heating means is varied to determine the effect on weight-loss of air treatment agent from the absorbent pad over time in use of the device. It can be seen that the greatest weight-loss is achieved when the heating means is located in a centralised position of the pad, whereas the weight-loss is reduced when the heating means is located at the side of the pad, and reduced further when located at the top of the pad and reduced yet further when located at the bottom of the pad.

Figure 3:
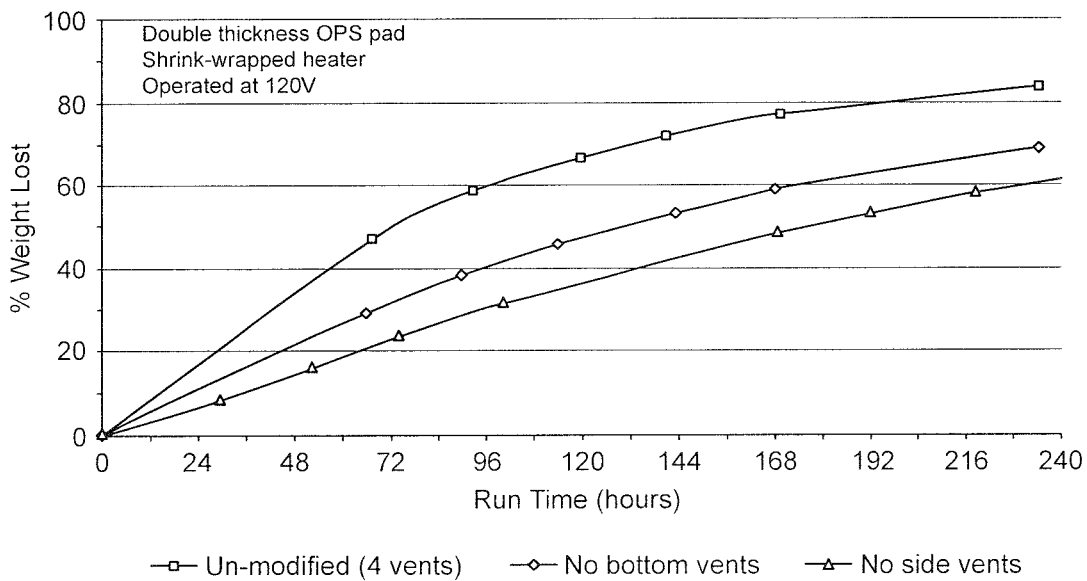
FIG. 3 shows a graph of performance variation associated with the presence or absence of vent holes in different locations.

Turning to FIG. 3 a weight-loss study is shown in which the position and number of the vent holes is varied to determine the effect on weight-loss of air treatment agent from the absorbent pad over time in use of the device. It can be seen that the greatest weight-loss is achieved when the vent holes are located at the top, the sides and the bottom of the housing, whereas the weight-loss is reduced when the vent holes at the bottom of the housing are sealed shut and the chimney effect is removed/ameliorated, and reduced further when the side vent holes are sealed shut and the airflow through the device is removed/ameliorated.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An emanation device comprising:
   a housing defining a sealed container having a front wall and a rear wall, each of the front wall and the rear wall defining a length and a width of the housing, and the front wall and the rear wall connected to each other by a top wall, a bottom wall and one or more side walls defining the depth of the housing, wherein the length and width are each greater than the depth;
   at least one vent hole in each of the top wall, the bottom wall and the, or each, side wall;
   electrical plug pins connected to the rear wall of the housing, said plug pins being operatively connected to a heating means located within the interior of the housing;
   an absorbent pad containing a quantity of air treatment agent mounted within the interior of the housing, wherein the pad is made from electrical conductive paper with the heating means formed from inlaid carbon;
   and wherein the pad fills a majority of the length and width of the housing.

2. An emanation device according to claim 1, wherein the heating means is in contact with a surface of the electrical conductive paper of the pad.

3. An emanation device according to claim 1, wherein the power consumption of the device is less than 2 W.

4. An emanation device according to claim 3 wherein the power consumption of the device is less than 1.5 W.

5. An emanation device according to claim 1, wherein the air treatment agent is a volatile liquid containing one or more of: a fragrance, a deodorizing material and/or a pest control material.

6. An emanation device according to claim 1, wherein at least a portion of the pad is in contact with at least one of: the top wall, the bottom wall and/or the side wall(s).

7. An emanation device according to claim 6, wherein at least a portion of the pad is in contact with at least two of: the top wall, the bottom wall and/or one or both side walls.

8. An emanation device according to claim 7, wherein at least a portion of the pad is in contact with bottom wall and both side walls.

9. An emanation device according to claim 1, wherein the device and the pad held therewithin is of a four sided shape.

10. An emanation device according to claim 1, wherein the vent holes are located such that when the plug pins are located in a mains electrical socket, the top vent hole(s) is located within the uppermost ⅓ of the top of the housing, the bottom vent hole(s) is located within the bottom ⅓ of the bottommost of the housing, and the side vent hole(s) is located within the nearest ⅓ of the side(s) of the housing.

11. An emanation device according to claim 1, wherein the vent holes are sized to extend at least 1 mm in any lateral direction whilst possessing a minimum area of 2 mm².

12. An emanation device according to claim 11, wherein no continuous area of any single vent hole has a radius of greater than 5 mm.

13. An emanation device according to claim 12, wherein no continuous area of any single vent hole has a radius greater than 4.5 mm.

14. An emanation device according to claim 1, wherein edges of the vent holes have a substantially rounded profile of continuous or variable curvature.

15. An emanation device according to claim 1, wherein one or more vent holes are provided in the front wall.

16. An emanation device according to claim 1, wherein the air treatment agent contains a dye and the rear wall is transparent or translucent to provide the device with a visual end of life mechanism.

17. An emanation device according to claim 1, wherein the device is configured to provide continuous emanation of the air treatment agent for 1 week.

* * * * *